(12) United States Patent
Han et al.

(10) Patent No.: US 11,713,350 B2
(45) Date of Patent: Aug. 1, 2023

(54) MEDICINE FOR TREATING DISORDERS OF GLUCOSE AND/OR LIPID METABOLISM AND A METHOD OF TREATING GLUCOSE AND/OR LIPID METABOLIC DISORDERS

(71) Applicant: Hefei University of Technology, Hefei (CN)

(72) Inventors: Jihong Han, Hefei (CN); Yajun Duan, Hefei (CN); Shuang Zhang, Hefei (CN); Xiaoxiao Yang, Hefei (CN); Yuanli Chen, Hefei (CN)

(73) Assignee: Hefei University of Technology, Hefei (CN)

( * ) Notice: Subject to any disclaimer, the term of this patent is extended or adjusted under 35 U.S.C. 154(b) by 321 days.

(21) Appl. No.: 16/991,192

(22) Filed: Aug. 12, 2020

(65) Prior Publication Data

US 2021/0087262 A1 Mar. 25, 2021

(30) Foreign Application Priority Data

Aug. 13, 2019 (CN) .......................... 201910742795.6

(51) Int. Cl.
| | |
|---|---|
| C07K 16/22 | (2006.01) |
| A61P 3/06 | (2006.01) |
| A61P 3/10 | (2006.01) |
| A61K 48/00 | (2006.01) |
| C12N 15/113 | (2010.01) |

(52) U.S. Cl.
CPC ............ *C07K 16/22* (2013.01); *A61K 48/005* (2013.01); *A61P 3/06* (2018.01); *A61P 3/10* (2018.01); *C12N 15/113* (2013.01); *C12N 2310/11* (2013.01); *C12N 2310/14* (2013.01)

(58) Field of Classification Search
CPC . A61K 48/005; A61P 3/06; A61P 3/10; C12N 15/113; C12N 2310/11; C12N 2310/14; C12N 2310/20
USPC ..................... 435/6.1, 91.1, 91.31, 455, 458; 514/44 A, 44 R; 536/23.1, 24.5
See application file for complete search history.

(56) References Cited

PUBLICATIONS

Zhang et al (Cell. Physiol. Biochem., vol. 43, pp. 1742-1754 (2017)) (Year: 2017).*
Zhang et al (Hepatology, vol. 53, No. 4, pp. 1306-1315 (2011)) (Year: 2011).*
Ricciardi et al (Nephrology Dialysis Transplantation, vol. 32, Supplement 3, iii99-iii101 (2017)) (Year: 2017).*
Garcia-Compean (World J. Gastroenterol., vol. 15, No. 3, pp. 280-288 (2009)). (Year: 2009).*
Teo et al., Extended-release niacin therapy and risk of ischemic stroke in patients with cardiovascular disease: the Atherothrombosis Intervention in Metabolic Syndrome with low HDL/High Triglycerides: Impact on Global Health Outcome (AIM-HIGH) trial. Stroke. Oct. 2013;44(10):2688-93.
Bruckert et al., Perspectives in cholesterol-lowering therapy: the role of ezetimibe, a new selective inhibitor of intestinal cholesterol absorption. Circulation. Jul. 1, 2003;107(25):3124-8.
Costet, Molecular pathways and agents for lowering LDL-cholesterol in addition to statins. Pharmacol Ther. Jun. 2010;126(3):263-78.
Della Badia et al., Targeting PCSK9 as a promising new mechanism for lowering low-density lipoprotein cholesterol. Pharmacol Ther. Aug. 2016;164:183-94.
Douros et al., Sulfonylureas as second line drugs in type 2 diabetes and the risk of cardiovascular and hypoglycaemic events: population based cohort study. BMJ. Jul. 18, 2018;362:k2693, 9 pages.
Durham et al., Hepatotoxicity upon using niacin to pass a drug test: A case report. J Am Pharm Assoc (2003). Sep.-Oct. 2018;58(5):564-567, pre-publication edition.
Fioretto et al., SGLT2 Inhibitors and the Diabetic Kidney. Diabetes Care. Aug. 2016;39 Suppl 2:S165-71.
Fitchett, A safety update on sodium glucose co-transporter 2 inhibitors. Diabetes Obes Metab. Apr. 2019;21 Suppl 2:34-42.
Foretz et al., Understanding the glucoregulatory mechanisms of metformin in type 2 diabetes mellitus. Nat Rev Endocrinol. Oct. 2019;15(10):569-589.
Frias et al., Efficacy and safety of LY3298176, a novel dual GIP and GLP-1 receptor agonist, in patients with type 2 diabetes: a randomised, placebo-controlled and active comparator-controlled phase 2 trial. Lancet. Nov. 17, 2018;392(10160):2180-2193.
Frier et al., Hypoglycaemia in diabetes mellitus: epidemiology and clinical implications. Nat Rev Endocrinol. Dec. 2014;10(12):711-22.
Giogliano et al., Clinical efficacy and safety of achieving very low LDL-cholesterol concentrations with the PCSK9 inhibitor evolocumab: a prespecified secondary analysis of the FOURIER trial. Lancet. Oct. 28, 2017;390(10106):1962-1971.
Hunter et al., Metformin reduces liver glucose production by inhibition of fructose-1-6-bisphosphatase. Nat Med. Sep. 2018;24(9):1395-1406.
Inagaki et al., SYR-472, a novel once-weekly dipeptidyl peptidase-4 (DPP-4) inhibitor, in type 2 diabetes mellitus: a phase 2, randomised, double-blind, placebo-controlled trial. Lancet Diabetes Endocrinol. Feb. 2014;2(2):125-32.
Liu et al., Statins: Adverse reactions, oxidative stress and metabolic interactions. Pharmacol Ther. Mar. 2019;195:54-84.
Mckeage et al., Fenofibrate: a review of its use in dyslipidaemia. Drugs. Oct. 1, 2011;71(14):1917-46.
Ooi et al., Effects of extended-release niacin on the postprandial metabolism of lipoprotein(a) and apolipoprotein B-100-containing lipoproteins in statin-treated men with type 2 diabetes. School of Medicine and Pharmacology, University of Western Australia. 30 pages, (2015).

(Continued)

*Primary Examiner* — Jane J Zara
(74) *Attorney, Agent, or Firm* — McCarter & English, LLP; Marcie B. Clarke; Dylan M. Blumenthal

(57) ABSTRACT

The present invention relates to a medicine for treating disorders of glucose and/or lipid metabolism. This invention demonstrates a new therapeutic target for treatment of glucose and/or lipid metabolic disorders. The invention further provides a method of treating glucose and/or lipid metabolic disorders, administering to a subject comprising a Nogo-B inhibitor, thereby treating the glucose and/or lipid metabolic disorders.

4 Claims, 6 Drawing Sheets

Specification includes a Sequence Listing.

(56) References Cited

PUBLICATIONS

Ou et al., Effects on Clinical Outcomes of Adding Dipeptidyl Peptidase-4 Inhibitors Versus Sulfonylureas to Metformin Therapy in Patients With Type 2 Diabetes Mellitus. Ann Intern Med. Nov. 3, 2015;163(9):663-72.
Robinson et al., Safety of Very Low Low-Density Lipoprotein Cholesterol Levels With Alirocumab: Pooled Data From Randomized Trials. J Am Coll Cardiol. Feb. 7, 2017;69(5):471-482.
Sabatine et al., Efficacy and safety of evolocumab in reducing lipids and cardiovascular events. N Engl J Med. Apr. 16, 2015;372(16):1500-9.
Soccio et al., Thiazolidinediones and the promise of insulin sensitization in type 2 diabetes. Cell Metab. Oct. 7, 2014;20(4):573-91.
Tahrani et al., Pharmacology and therapeutic implications of current drugs for type 2 diabetes mellitus. Nat Rev Endocrinology. Jun. 24, 2016;12:566-592.
Tirkkonen et al., Frequency and clinical relevance of drug interactions with lovastatin and simvastatin: an observational database study. Drug Saf. 2008;31(3):231-40.

\* cited by examiner

SEQUENCE LISTING

<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: Target sequence

<400> SEQUENCE: 1
gtatctcctc ttgcgaggg                                                  19

<210> SEQ ID NO 2
<211> LENGTH: 23
<212> TYPE: DNA
<213> ORGANISM: Artificial Sequence
<220> FEATURE:
<223> OTHER INFORMATION: Target sequence

<400> SEQUENCE: 2
gatgtccaga tatagcttag ggg                                             23

<210> SEQ ID NO 3
<211> LENGTH: 20
<212> TYPE: DNA
<213> ORGANISM: Artificial Sequence
<220> FEATURE:
<223> OTHER INFORMATION: Target sequence

<400> SEQUENCE: 3
gatgatggtc tcgcccttgg                                                 20

<210> SEQ ID NO 4
<211> LENGTH: 22
<212> TYPE: DNA
<213> ORGANISM: Artificial Sequence
<220> FEATURE:
<223> OTHER INFORMATION: Target sequence

<400> SEQUENCE: 4
agttaatgct ggcctcagaa gg                                              22

<210> SEQ ID NO 5
<211> LENGTH: 21
<212> TYPE: DNA
<213> ORGANISM: Artificial Sequence
<220> FEATURE:
<223> OTHER INFORMATION: Synthetic siRNA

<400> SEQUENCE: 5
ggaucucauu guagucauat t                                               21

<210> SEQ ID NO 6
<211> LENGTH: 21
<212> TYPE: DNA
<213> ORGANISM: Artificial Sequence
<220> FEATURE:
<223> OTHER INFORMATION: Synthetic siRNA

<400> SEQUENCE: 6
uaugacuaca augagauccT t                                               21

<210> SEQ ID NO 7
<211> LENGTH: 23
<212> TYPE: DNA
<213> ORGANISM: Artificial Sequence

```
<220> FEATURE:
<223> OTHER INFORMATION: Synthetic siRNA

<400> SEQUENCE: 7
gcaguguuga ugugggauauu utt                                              23

<210> SEQ ID NO 8
<211> LENGTH: 23
<212> TYPE: DNA
<213> ORGANISM: Artificial Sequence
<220> FEATURE:
<223> OTHER INFORMATION: Synthetic siRNA

<400> SEQUENCE: 8
aaauacccac aucaacacug ctt                                               23

<210> SEQ ID NO 9
<211> LENGTH: 21
<212> TYPE: DNA
<213> ORGANISM: Artificial Sequence
<220> FEATURE:
<223> OTHER INFORMATION: Synthetic siRNA

<400> SEQUENCE: 9
cacauaaacu aggaagagat t                                                 21

<210> SEQ ID NO 10
<211> LENGTH: 21
<212> TYPE: DNA
<213> ORGANISM: Artificial Sequence
<220> FEATURE:
<223> OTHER INFORMATION: Synthetic siRNA

<400> SEQUENCE: 10
ucucuuccua guuuaugugt t                                                 21

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
catgcctggg ttatggagac ct                                                22

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ccgtaaccaa gggagtgtcc c                                                 21

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
aggtgccctt attgcttcca                                                   20
```

```
<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
ttgtgagaga ccacatcggt g                                         21

<210> SEQ ID NO 15
<211> LENGTH: 23
<212> TYPE: DNA
<213> ORGANISM: Artificial Sequence
<220> FEATURE:
<223> OTHER INFORMATION: Synthetic siRNA

<400> SEQUENCE: 15
uucuccgaac gugucacgud tdt                                       23

<210> SEQ ID NO 16
<211> LENGTH: 23
<212> TYPE: DNA
<213> ORGANISM: Artificial Sequence
<220> FEATURE:
<223> OTHER INFORMATION: Synthetic siRNA

<400> SEQUENCE: 16
acgugacacg uucggagaad tdt                                       23
```

MEDICINE FOR TREATING DISORDERS OF GLUCOSE AND/OR LIPID METABOLISM AND A METHOD OF TREATING GLUCOSE AND/OR LIPID METABOLIC DISORDERS

CROSS-REFERENCE TO RELATED APPLICATIONS

This application claims the benefit of priority of Chinese Application No. 201910742795.6 filed on Aug. 13, 2019, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Oct. 23, 2020, is named 132257_00102_SL.txt and is 3,365 bytes in size.

TECHNICAL FIELD OF THE INVENTION

This invention belongs to the field of biomedical technology, and specifically relates to a medicine for treating disorders of glucose and/or lipid metabolism, wherein the medicine contains a Nogo-B inhibitor, and a method of treating glucose and/or lipid metabolic disorders, administering to a subject comprising a Nogo-B inhibitor, thereby treating the glucose and/or lipid metabolic disorders.

BACKGROUND OF THE INVENTION

As the main source of human energy supply, glucose and/or lipid metabolism plays an essential role in our life activities. However, associated with improved living standards, the disorders of glucose and/or lipid metabolism are very common. The disorders of glucose and/or lipid metabolism generally cause a series of diseases such as hyperlipidemia, diabetes, fatty liver, obesity, arteriosclerotic cardiovascular and cerebrovascular diseases, etc. The long-term abnormal glucose and/or lipid levels will harm organs of our body and lead to the gradual decline of the organ functions, which is a main cause of diseases, disability and death of patients.

The drugs currently used for lowering blood sugar include: Metformin, which is the first-line drug for the treatment of type 2 diabetes. Its role is to reduce glucose production in the liver, improve the body's sensitivity to insulin, so that the body uses insulin more effectively (Hunter R W, Hughey C C, Lantier L, Sundelin E I, Peggie M, Zeqiraj E, et al. Metformin reduces liver glucose production by inhibition of fructose-1-6-bisphosphatase. *Nat Med* 2018; 24:1395-1406; Foretz M, Guigas B, Viollet B. Understanding the glucoregulatory mechanisms of metformin in type 2 diabetes mellitus. *Nat Rev Endocrinol* 2019; 15:569-589). Sulfonylureas can stimulate the body to produce more insulin. However, the possible side effects of sulfonylurea include hypoglycemia and weight gain (Douros A, Dell'Aniello S, Yu O H Y, Filion K B, Azoulay L, Suissa S. Sulfonylureas as second line drugs in type 2 diabetes and the risk of cardiovascular and hypoglycaemic events: population based cohort study. *BMJ* 2018; 362:k2693; Tahrani A A, Barnett A H, Bailey C J. Pharmacology and therapeutic implications of current drugs for type 2 diabetes mellitus. *Nat Rev Endocrinol* 2016; 12:566-592). Thiazolidinediones can increase insulin sensitivity in human tissues, thus they are also used in the treatment of type 2 diabetes. Unfortunately, the severe side effects of thiazolidinediones have been reported (Soccio R E, Chen E R, Lazar M A. Thiazolidinediones and the promise of insulin sensitization in type 2 diabetes. *Cell Metab* 2014; 20:573-591). DPP-4 inhibitors can reduce blood glucose levels, but the protective effect is modest. Although DPP-4 inhibitors do not lead to weight gain, they may cause joint pain and increase the risk of atherosclerosis (Inagaki N, Onouchi H, Sano H, Funao N, Kuroda S, Kaku K. SYR-472, a novel once-weekly dipeptidyl peptidase-4 (DPP-4) inhibitor, in type 2 diabetes mellitus: a phase 2, randomised, double-blind, placebo-controlled trial. *Lancet Diabetes Endocrinol* 2014; 2:125-132; Ou S M, Shih C J, Chao P W, Chu H, Kuo S C, Lee Y J, et al. Effects on clinical outcomes of adding dipeptidyl peptidase-4 inhibitors versus sulfonylureas to metformin therapy in patients with type 2 diabetes mellitus. *Ann Intern Med* 2015; 163:663-672). GLP-1 receptor agonists, which slow digestion and help lower blood sugar levels, may have side effects including nausea and increased risk of pancreatitis (Frias J P, Nauck M A, Van J, Kutner M E, Cui X, Benson C, et al. Efficacy and safety of LY3298176, a novel dual GIP and GLP-1 receptor agonist, in patients with type 2 diabetes: a randomised, placebo-controlled and active comparator-controlled phase 2 trial. *Lancet* 2018; 392:2180-2193). SGLT2 inhibitors prevent kidneys from absorbing sugar back into the blood. The side effects of SGLT2 inhibitors may include genital fungal infections, urinary tract infections, hypotension, and high risk of diabetic ketoacidosis (Fioretto P, Zambon A, Rossato M, Busetto L, Vettor R. SGLT2 Inhibitors and the Diabetic Kidney. *Diabetes Care* 2016; 39 Suppl 2:S165-171; Fitchett D. A safety update on sodium glucose co-transporter 2 inhibitors. *Diabetes Obes Metab* 2019; 21 Suppl 2:34-42). Insulin is an ideal treatment for diabetes, and hypoglycemia may be the side effect (Frier B M. Hypoglycaemia in diabetes mellitus: epidemiology and clinical implications. *Nat Rev Endocrinol* 2014; 10:711-722).

The lipid lowering medicines include the medicines for reducing low-density lipoprotein cholesterol levels and reducing triglyceride levels. Low-density lipoprotein cholesterol can be reduced by statins, which block the production of cholesterol in the liver while enhance the clearance of cholesterol from the blood in the liver. However, statins are not effective for many people (Liu A, Wu Q, Guo J, Ares I, Rodriguez J L, Martinez-Larranaga M R, et al. Statins: Adverse reactions, oxidative stress and metabolic interactions. *Pharmacol Ther* 2019; 195:54-84; Goldberg A C, Leiter L A, Stroes E S G, Baum S J, Hanselman J C, Bloedon L T, et al. Effect of bempedoic acid vs placebo added to maximally tolerated statins on low-density lipoprotein cholesterol in patients at high risk for cardiovascular disease: The CLEAR Wisdom Randomized Clinical Trial. *JAMA* 2019; 322:1780-1788). The cholesterol absorption inhibitors, such as ezetimibe, can lower blood cholesterol by limiting the absorption of dietary cholesterol (Bruckert E, Giral P, Tellier P. Perspectives in cholesterol-lowering therapy: the role of ezetimibe, a new selective inhibitor of intestinal cholesterol absorption. *Circulation* 2003; 107: 3124-3128). PCSK9 inhibitors are new class of medicine to help the liver to absorb more low-density lipoprotein cholesterol, thereby reducing the levels of circulating cholesterol (Della Badia L A, Elshourbagy N A, Mousa S A. Targeting PCSK9 as a promising new mechanism for lowering low-density lipoprotein cholesterol. *Pharmacol Ther* 2016; 164:183-194). The medicines of PCSK9 inhibitors are mainly PCSK9 monoclonal antibodies, such as Alirocumab (Praluent, Robinson J G, Rosenson R S, Farnier M, et al.

Safety of very low low-density lipoprotein cholesterol levels with alirocumab: pooled data from randomized trials. *J Am Coll Cardiol* 2017; 69:471-82) and evolocumab (repata, Sabatine M S, Giugliano R P, Wiviott S D, Raal F J, Blom D J, Robinson J, Ballantyne C M, Somaratne R, Legg J, Wasserman S M, Scott R, Koren M J, Stein E A; Open-Label Study of Long-Term Evaluation against LDL Cholesterol (OSLER) Investigators. Efficacy and safety of evolocumab in reducing lipids and cardiovascular events. *N Engl J Med.* 2015; 372:1500-9). PCSK9 inhibitors can be used in patients who have a genetic condition that causes very high levels of low-density lipoprotein cholesterol or patients with coronary disease who have intolerance to statins or other cholesterol-lowering medications (Costet P. Molecular pathways and agents for lowering LDL-cholesterol in addition to statins. *Pharmacol Ther* 2010; 126:263-278; Giugliano R P, Pedersen T R, Park J G, De Ferrari G M, Gaciong Z A, Ceska R, et al. Clinical efficacy and safety of achieving very low LDL-cholesterol concentrations with the PCSK9 inhibitor evolocumab: a prespecified secondary analysis of the FOURIER trial. *Lancet* 2017; 390:1962-1971).

The anti-hypertriglyceridemia medicines are fibrates, such as fenofibrate (TriCor, Fenoglide, etc) and Gemfibrozil (Lopid). They can reduce the production of very low-density lipoprotein (VLDL) cholesterol (VLDL, which is very rich in triglycerides) in the liver and accelerate the clearance of triglycerides in the blood. However, the combination of fibrates and statins increases the risk of side effects of statins (McKeage K, Keating G M. Fenofibrate: a review of its use in dyslipidaemia. Drugs 2011; 71:1917-1946; Tirkkonen T, Ryynanen A, Vahlberg T, Irjala K, Klaukka T, Huupponen R, et al. Frequency and clinical relevance of drug interactions with lovastatin and simvastatin: an observational database study. *Drug Saf* 2008; 31:231-240). Niacin limits the capacity of liver to produce low-density lipoprotein and VLDL cholesterol, but niacin does not provide more benefits than statins, and niacin may increase risk of liver injury and stroke (Ooi E M, Watts G F, Chan D C, Pang J, Tenneti V S, Hamilton S J, et al. Effects of extended-release niacin on the postprandial metabolism of Lp(a) and ApoB-100-containing lipoproteins in statin-treated men with type 2 diabetes mellitus. *Arterioscier Thromb Vasc Biol* 2015; 35:2686-2693; Durham S H, Covington E W, Clemmons K J. Hepatotoxicity upon using niacin to pass a drug test: A case report. *J Am Pharm Assoc* (2003) 2018; 58:564-567; Teo K K, Goldstein L B, Chaitman B R, Grant S, Weintraub W S, Anderson D C, et al. Extended-release niacin therapy and risk of ischemic stroke in patients with cardiovascular disease: the Atherothrombosis Intervention in Metabolic Syndrome with low HDL/High Triglycerides: Impact on Global Health Outcome (AIM-HIGH) trial. Stroke 2013; 44:2688-2693).

Taken together, the current strategies to treat glucose and/or lipid metabolic disorders are still limited in controlling blood glucose levels and blood lipids profiles, which are unable to target the process of glucose and/or lipid transformation. Carbohydrate response element binding protein (ChREBP) is a transcription factor playing an important role in regulation of glucose and/or lipid metabolism. However, the simple inhibition or activation of ChREBP alone does not improve glucose and/or lipid metabolism. Instead, regulation of ChREBP expression/activity based on the dynamic pathological process can lead to better execution of its functions.

Reticulon 4 (RTN4), also known as Nogo proteins, is localized in the endoplasmic reticulum and related to endoplasmic reticulum duct membrane hyperplasia and membrane curvature. RTN4 family includes three subtypes: Nogo-A, B and C. Nogo-B is also the only subtype that can be detected in the circulation and is mainly synthesized and secreted by the liver. The expression of Nogo-B in liver is associated with alcoholic liver disease and liver fibrosis, but if Nogo-B is a target for treating glucose and/or lipid metabolic disorders remains unknown.

SUMMARY OF THE INVENTION

The inventors found through research that RTN4B (Nogo-B) inhibitor stimulates ChREBP to achieve benign fat accumulation under physiological conditions, but under the pathological state of glucose and/or lipid metabolism disorders (that is, excessive intake of carbohydrates leads to abnormal metabolism of the body, and liver damage is the main sign) inhibit ChREBP, so as to avoid excessive accumulation of lipids causing body damage.

The inventors of this application found that RTN4B (Nogo-B) inhibitor can activate ChREBP expression at the physiological state, which results in a mild lipid accumulation in the liver under physiological conditions. However, at the pathological state with glucose and/or lipid metabolic disorders (i.e., the over intake of high-carbohydrate food/drinking can lead to abnormal metabolism in the body, with liver injury as the main markers), Nogo-B inhibitor reduced ChREBP expression/activity, so as to avoid excessive accumulation of lipids to cause body damage. At present, no target or medicine has been found to improve glucose and/or lipid metabolism based on the physiological and pathological conditions above. Therefore, based on the clear correlation between RTN4B (Nogo-B) gene expression levels and protein levels and glucose/lipid metabolic disorders, we completed this invention.

First provided herein is a medicine for treating disorders of glucose and/or lipid metabolism, wherein the medicine contains a Nogo-B inhibitor mentioned above.

Specifically, the Nogo-B inhibitor is an inhibitor that reduces Nogo-B mRNA level and/or Nogo-B protein level and/or Nogo-B protein function. More specifically, the Nogo-B inhibitor includes at least one of follows: Nogo-B antisense oligonucleotide, Nogo-B siRNA, Nogo-B short hairpin RNA, Nogo-B monoclonal antibody, small molecule inhibitor of Nogo-B, nucleic acid molecule targeting Nogo-B for gene editing and Nogo-B vaccine.

Preferably, the Nogo-B inhibitor is nucleic acid molecules targeting Nogo-B for gene editing, further comprising a reagents gene editing operation. Furthermore, the target DNA for the gene editing is exon 2 and exon 8 of Nogo-B gene. In one particular embodiment, the oligonucleotide sequences for the target DNA are as follows: GTATCTCCTCTTGCGAGGG (SEQ ID NO: 1), GATGTCCAGATATAGCTTAGGGG (SEQ ID NO: 2), GATGATGGTCTCGCCCTTGG (SEQ ID NO: 3), AGTTAATGCTGGCCTCAGAAGG (SEQ ID NO:4). Alternatively, the Nogo-B inhibitor is a Nogo-B monoclonal antibody, specifically mouse/rabbit derived/humanized anti-human Nogo-B antibodies.

In addition, preferably, the Nogo-B inhibitor is small interfering RNAs, specifically three pairs of small interfering RNAs with the following sequences:

1st pair

```
                                             (SEQ ID NO: 5)
GGAUCUCAUUGUAGUCAUAUU
and
                                             (SEQ ID NO: 6)
UAUGACUACAAUGAGAUCCTT;
```

2nd pair

```
                                             (SEQ ID NO: 7)
GCAGUGUUGAUGUGGGUAUUUTT
and
                                             (SEQ ID NO: 8)
AAAUACCCACAUCAACACUGCTT;
or
```

3rd pair

```
                                             (SEQ ID NO: 9)
CACAUAAACUAGGAAGAGATT
and
                                             (SEQ ID NO: 10)
UCUCUUCCUAGUUUAUGUGTT.
```

Provided herein is a method of treating glucose and/or lipid metabolic disorders, administering to a subject comprising a Nogo-B inhibitor, thereby treating the glucose and/or lipid metabolic disorders.

Preferably, the RTN4B (Nogo-B) inhibitor is an inhibitor that reduces RTN4B (Nogo-B) mRNA and/or RTN4B (Nogo-B) protein levels and/or Nogo-B protein function.

All of the substances in the art that can reduce RTN4B (Nogo-B) mRNA and/or RTN4B (Nogo-B) protein levels can be used as RTN4B (Nogo-B) inhibitors of the present invention, such as RTN4B (Nogo-B) antisense oligonucleotides, RTN4B (Nogo-B) small interfering RNAs (siRNAs), RTN4B (Nogo-B) short hairpin RNAs (shRNAs), RTN4B (Nogo-B) monoclonal antibodies, small molecule inhibitors of Nogo-B, nucleic acid molecules targeting Nogo-B for gene editing, and RTN4B (Nogo-B) vaccines.

Preferably, the Nogo-B inhibitor is nucleic acid molecules targeting Nogo-B for gene editing, further comprises a reagent for gene editing operations. Furthermore, target DNA for the gene editing is exon 2 and exon 8 of Nogo-B gene. In one particular embodiment, the oligonucleotide sequences for the target DNA are as follows: GTATCTCCTCTTGCGAGGG (SEQ ID NO: 1), GATGTCCAGATATAGCTTAGGGG (SEQ ID NO: 2), GATGATGGTCTCGCCCTTGG (SEQ ID NO: 3), AGTTAATGCTGGCCTCAGAAGG (SEQ ID NO: 4).

In addition, preferably, the Nogo-B inhibitor is small interfering RNAs, specifically three pairs of small interfering RNAs with the following sequences:

1st pair

```
                                             (SEQ ID NO: 5)
GGAUCUCAUUGUAGUCAUAUU
and
                                             (SEQ ID NO: 6)
UAUGACUACAAUGAGAUCCTT;
```

2nd pair

```
                                             (SEQ ID NO: 7)
GCAGUGUUGAUGUGGGUAUUUTT
and
                                             (SEQ ID NO: 8)
AAAUACCCACAUCAACACUGCTT;
or
```

3rd pair

```
                                             (SEQ ID NO: 9)
CACAUAAACUAGGAAGAGATT
and
                                             (SEQ ID NO: 10)
UCUCUUCCUAGUUUAUGUGTT.
```

Preferably, the Nogo-B inhibitor is a Nogo-B monoclonal antibody. More preferably, the Nogo-B inhibitor is mouse/rabbit derived/humanized anti-human Nogo-B antibody.

The disorders of glucose and/or lipid metabolism refer to hyperlipidemia, diabetes, fatty liver, obesity, or arteriosclerotic cardiovascular or cerebrovascular disease.

This invention also provides a kit for auxiliary diagnosis, progress analysis, curative effect judgment and prognosis evaluation of glucose and/or lipid metabolic disorders. The kit can contain mouse/rabbit derived/humanized anti-human Nogo-B antibody, rabbit or sheep anti-mouse or sheep anti-rabbit antibody and 3,3,5,5-tetramethylbenzidine.

In addition, the invention also provides a method for preventing the disorders of glucose and/or lipid metabolism by gene editing, i.e., adopting gene editing to prepare transgenic animals. Further, the gene editing is CRISPR/cas9 gene editing technology, and preferably, the target DNA is exon 2 and exon 8 of Nogo-B gene. In one particular embodiment, the oligonucleotide sequences for the target DNA are as follows:

```
                                             (SEQ ID NO: 1)
            GTATCTCCTCTTGCGAGGG, (SEQ ID NO: 2)
            GATGTCCAGATATAGCTTAGGGG, (SEQ ID NO: 3)
            GATGATGGTCTCGCCCTTGG, (SEQ ID NO: 4)
            AGTTAATGCTGGCCTCAGAAGG.
```

Or preferably, the Nogo-B inhibitor is the small interfering RNAs, specifically three pairs of small interfering RNAs with the following sequences: 1st pair: GGAUCUCAUUGUAGUCAUAUU (SEQ ID NO: 5) and UAUGACUACAAUGAGAUCCTT (SEQ ID NO: 6); 2nd pair: GCAGUGUUGAUGUGGGUAUUUTT (SEQ ID NO: 7) and AAAUACCCACAUCAACACUGCTT (SEQ ID NO: 8); or 3rd pair: CACAUAAACUAGGAAGAGATT (SEQ ID NO: 9) and UCUCUUCCUAGUUUAUGUGTT (SEQ ID NO: 10).

In conclusion, this invention can be used as an important new therapeutic target for treatment of disorders of glucose and/or lipid metabolism. The invention can further be used in preparation of monotherapy or combination therapies containing RTN4B (Nogo-B) inhibitor for treatment of various types of diseases related to glucose and/or lipid metabolic disorders. Thus, this invention provides a new option for treating glucose and/or lipid metabolic diseases.

DETAILED DESCRIPTION OF THE EMBODIMENTS

The embodiments of the invention are described in detail below. The embodiments are implemented on the premise of the technical solutions of the invention, and the detailed embodiments and specific procedures are given. However, the protection scope of the invention is not limited to the following Examples.

Figure 1:
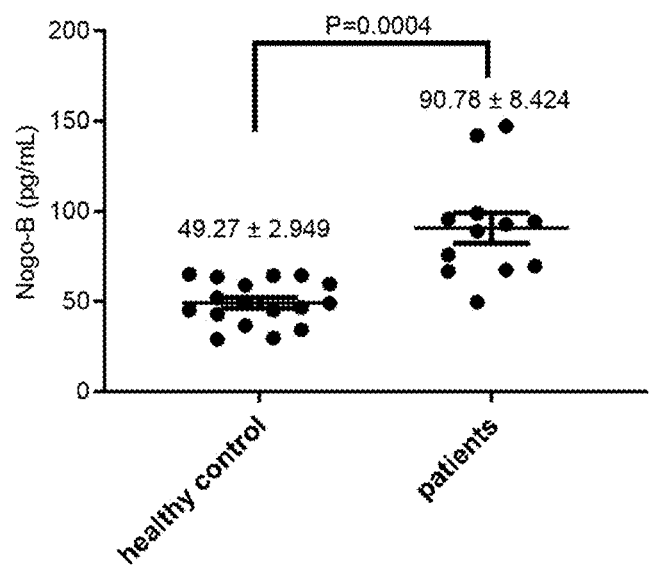
FIG. 1 shows the levels of Nogo-B protein expression in serum of patients with glucose and/or lipid metabolic disorder and healthy controls.

Example 1: Study of High Nogo-B Expression in Serum of Patients with Glucose and/or Lipid Metabolic Disorders After the serum of patients with glucose and/or lipid metabolic disorders and the serum of healthy volunteers were subpackaged without distinguishing the patients and volunteers, and only the serial numbers were marked, and the Nogo-B level was detected by specialized staff who were blinded to the groups represented by the serial numbers by using a kit. Among the collected samples, serum Nogo-B levels in 17 healthy volunteers and 12 patients with glucose and/or lipid metabolic disorders were detected. The ELISA kits were purchased from Wuhan Cusabio (CSB-EL020572HU) Company. The results showed that the levels of Nogo-B protein in serum of patients with glucose and/or lipid metabolic disorder (90.78±8.424 pg/ml) were significantly higher than that in healthy controls (49.27±2.949 pg/ml), p<0.001 represents significant difference (FIG. 1).

Figure 2:
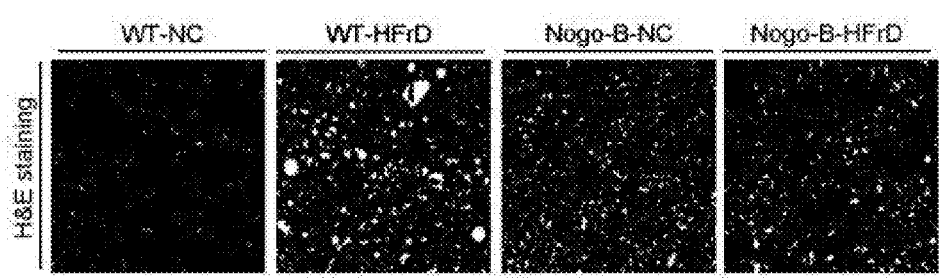
FIG. 2 shows the liver tissue sections of mice with inhibited Nogo-B expression by CRISPR/cas9 and control mice fed normal chow or the high-fructose diet for 2 weeks.

Example 2: Study of the Effect of Inhibition of Nogo-B Expression on Mice Fed with High-Fructose Diet The expression of Nogo-B in mice was inhibited by CRISPR/cas9 technology and the mice and normal mice were divided into two groups respectively. One group continued to feed with normal chow (i.e., Nogo-B-NC group or WT-NC group), and the other group were fed with high-fructose diet (i.e. Nogo-B-HFrD group or WT-HFrD group), high-fructose diet contained 70% fructose. Two weeks later, the mice were sacrificed and sections of liver tissue were prepared for analysis. As shown in FIG. 2, the liver tissue of normal mice group fed with high-fructose diet (WT-HFrD) was damaged, which was manifested by the appearance of large lipid vacuoles and hepatocyte ballooning in the liver tissue, while mice group whose Nogo-B expression were inhibited fed with high-fructose diet (Nogo-B-HFrD) basically caused no damage. In addition, WT-NC and Nogo-B-NC in the figure are liver slices of mice group whose Nogo-B expression was inhibit by CRISPR/Cas9 technology and normal mice group fed with normal chow, showing that inhibiting Nogo-B expression in mice had an effect on the liver.

Figure 3:
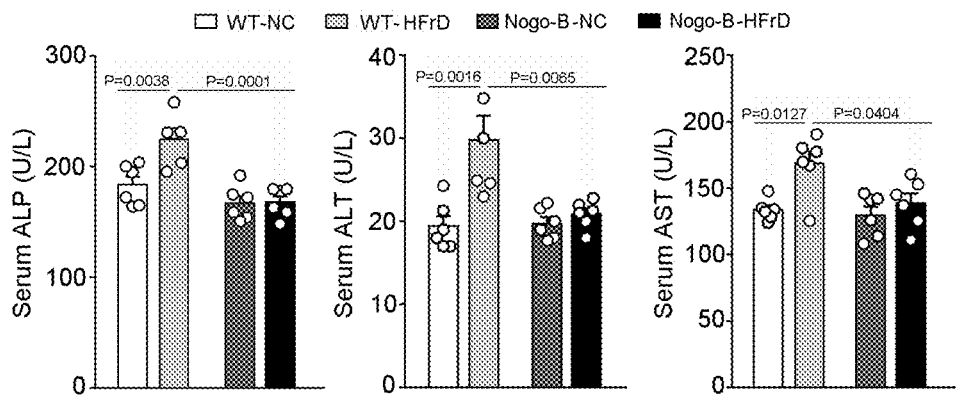
FIG. 3 shows the test results of enzyme activity characterizing liver function in serum in mice with inhibited Nogo-B expression by CRISPR/cas9 and control mice fed normal chow or the high-fructose diet for 2 weeks.

The serum of the above-mentioned mice was subjected to the enzyme activity analysis of liver function, and the results were shown in FIG. 3. Among them, it was shown that in the normal mice fed with high-fructose diet (WT-HFrD), liver injury indicators, alkaline phosphatase ALP, alanine aminotransferase ALT, and aspartate aminotransferase AST were significantly increased (WT-HFrD vs. WT-NC); while mice group whose Nogo-B expression were inhibited fed with high-fructose diet (Nogo-B-HFrD) basically had no changes in these indicators, indicating that high-fructose food basically did not cause damage (Nogo-B-HFrD vs. Nogo-B-NC). In addition, in FIG. 3, WT-NC and Nogo-B-NC were respectively liver function enzyme activity analysis for mice group whose Nogo-B expression was inhibited by CRISPR/Cas9 technology and normal mice group fed with normal chow, showing inhibition of Nogo-B expression had no effect on mouse liver function enzyme activity (Nogo-B-NC vs. WT-NC).

Wherein, the method of CRISPR/cas9 technology to inhibit Nogo-B expression in mice was provided as follows:

1) Vector design, construction and purification: MIT CRISPR design tool (http://crisprmit.edu/) was used. According to the score, a pair of 20 bp oligonucleotide sequences against the target DNA were designed to prepare sgRNA, and primers were designed in the target region for subsequent gene identification in the mice.

The target DNA was exon 2 and exon 8 of Nogo-B gene. The sequences of the four oligonucleotides designed for target DNA were: GTATCTCCTCTTGCGAGGG (SEQ ID NO: 1), GATGTCCAGATATAGCTTAGGGG (SEQ ID NO: 2), GATGATGGTCTCGCCCTTGG (SEQ ID NO: 3), AGTTAATGCTGGCCTCAGAAGG (SEQ ID NO: 4). Under the action of U6 promoter, the four oligonucleotides targeted the target DNA to knockout the target gene.

Figure 4:
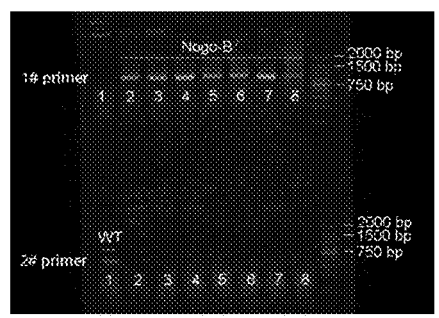
FIG. 4 Identification of Nogo-B knockout mice. Among them, the band 1 was result of control mice or wild-type mice, abbreviated as WT mice, and bands 2-8 were the results of the rice for which CRISPR/Cas9 technology was used to inhibit Nogo-B expression, abbreviated as Nogo-B$^{-/-}$ mice, DL2000 marker was on the right.

Two single stranded oligonucleotides (sgRNAs) were synthesized and annealed at 95° C. for 5 min and cooled naturally to room temperature to form double stranded DNA, which were linked with pGK1.1 linear vector using T4 DNA ligase. SgRNA expression vector was constructed. The recombinant plasmid was transformed into DH5☐ competent cells. Through the kanamycin resistance of the pGK1.1 linear vector and the sequencing of the target DNA, the positive clone plasmids were screened and identified, the correct colony clones were selected, and the plasmids were extracted after expansion and cultured to prepare in vitro transcription templates;

2) In vitro transcription: the sgRNA expression vector was linearized by Dra I enzyme, extracted and purified by phenol-chloroform, dissolved in nuclease-free water as the template for in vitro transcription. SgRNA was synthesized by T7 RNA polymerase in accordance with MEGAshortscript Kit (Ambion, AM1354) in vitro;

3) Microinjection of Cas9/sgRNA: the transcribed sgRNA and cas9 were mixed and the injection concentration was adjusted. The mixture was microinjected into the cytoplasm of fertilized eggs of C57BL/6 experimental mice by TE2000U microinjection instrument, and then the fertilized eggs were transplanted into the uterus of other C57BL/6 female mice with putative pregnancy, waiting for the birth of F0 mice;

4) Identification of F0 mice: 5-7 days after birth, Toe-cutting method was used to label F0 mice, and the cut tail tissues were subjected to phenol-chloroform method to extract DNA. According to the primers designed in the target region in the above experiment 1), two pairs of primers were used for the identification of Nogo-B knockout in mice, and the sequences were as follows: 1 # pair of primers: 2260Rtn4-gtF4: CATGCCTGGGTTATGGAGACCT (SEQ ID NO: 11), 2260Rtn4-gtR4: CCGTAACCAAGGGAGTGTCCC (SEQ ID NO: 12); 2 # pair of primers: 2260Rtn4-delgtF2: AGGTGCCCTTATTGCTTCCA (SEQ ID NO: 13), 2260Rtn4-delgtR2: TTGTGAGAGACCACATCGGTG (SEQ ID NO: 14). Among them, the PCR product of #1 pair of primers was too large (38 kb) in wild-type (WT) mice, so no bands could be seen in the electropherogram. The length of the PCR product in knockout (Nogo-B$^{-/-}$) mice was 870 bp; the PCR product of #2 pair of primers was 421 bp in WT mice, and 0 bp in Nogo-B$^{-/-}$ mice, and no band was visible. The PCR identification results were shown in FIG. 4. As shown in FIG. 4, No. 1 band was the PCR result of WT mice, No. 2-8 bands were the PCR result of Nogo-B$^{-/-}$ mice, and DL2000 marker was on the right. PCR-positive samples were selected for sequencing to ensure that the F0 generation mice with the correct sequence were selected.

5) Heritability test of F0 generation mice: the F0 generation mice with correct PCR product and sequence were mated with wild type C57BL/6 mice to produce F1 generation mice. The F1 mice were identified according to the identification method of F0 generation mice, and the positive F1 generation heterozygote mice obtained could be stably inherited. The mice after F4 generation were used for the experiment.

Example 3: Study of the Effect of Inhibition of Nogo-B Expression on Mice Fed with High-Glucose Diet In addition to high-fructose diet-induced tissue injury, over intake of high-glucose diet for a long time also causes glucose and/or lipid metabolic disorders. Therefore, we designed this example. In this example, CRISPR/cas9 technology was used to inhibit Nogo-B expression in mice, and the specific operation was the same as the process described in Example 2.

The CRISPR/cas9 technique was used (the targets were exon 2 and exon 8, which deleted 37 kb in genome and 2824 bp in transcriptome respectively) to inhibit mouse Nogo-B expression. The mice and normal mice were divided into two groups respectively. One group continued to feed with normal chow (i.e., Nogo-B-NC group or WT-NC group), and the other group were fed with high-glucose diet (i.e. Nogo-B-HGD group or WT-HGD group). The product number and source of the high-glucose diet are Cat # of MD17120502 and from BIOPIKE, Shanghai, China. Glucose tolerance test (GTT) and insulin tolerance test (ITT) were performed at the 9th week and the 10th week of HGD feeding respectively. At the beginning of the 11th week of HGD feeding, mice were sacrificed and serum samples were collected for analysis of liver function enzyme activity.

Figure 5A:
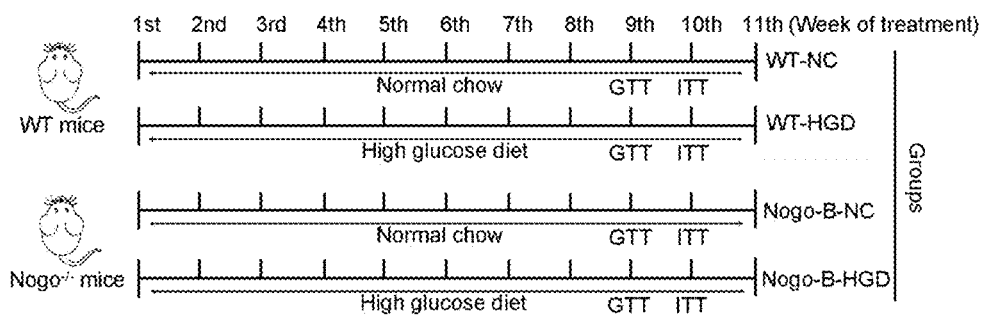
FIG. 5A shows the model diagram of treatments in mice with inhibited Nogo-B expression by CRISPR/cas9 and control mice, in which the group of control mice fed normal chow were named WT-NC group, the group of mice with inhibited Nogo-B expression by CRISPR/cas9 fed normal chow were named Nogo-B-NC group, the group of control mice fed the high-glucose diet were named WT-HGD, and the group of mice with inhibited Nogo-B expression by CRISPR/cas9 fed the high-glucose diet were named Nogo-B-HGD group.
Figure 5B:
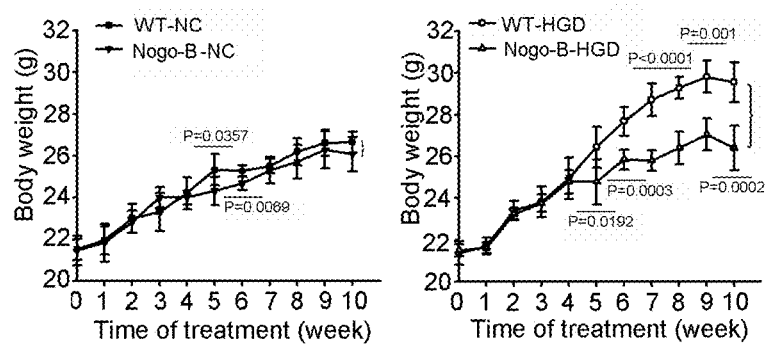
FIG. 5B shows the body weight gain of two groups of mice fed normal chow (WT-NC and Nogo-B-NC groups) (left) or two groups of mice fed the high-glucose diet (WT-HGD and Nogo-B-HGD groups) (right).
Figure 5C:
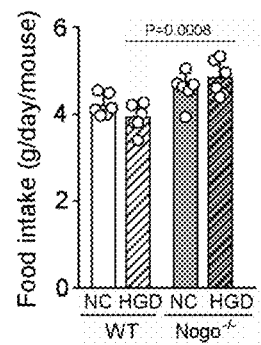
FIG. 5C shows the results of food intake of the four groups. Due to layout restrictions, Nogo in FIG. 5C represents Nogo-B.

FIG. 5A is a schematic diagram of the group of mice in which CRISPR/Cas9 technology was used to inhibit Nogo-B expression and the normal mouse group fed with normal chow or high-glucose diet. The normal mouse group fed with normal chow was named WT-NC, the group of in which CRISPR/Cas9 technology was used to inhibit Nogo-B expression fed with normal chow was named Nogo-B-NC group, normal mouse group fed with high-glucose diet was named WT-HGD, the group of in which CRISPR/Cas9 technology was used to inhibit Nogo-B expression fed with high-glucose diet was named Nogo-B-HGD. From the beginning to the end of the experiment, the weight and food intake of the mice were recorded every week. The results in FIG. 5B show that there was no difference in bodyweight gain between the two groups fed normal chow (WT-NC and Nogo-B-NC), but the bodyweight of mice in WT-HGD group increased more than Nogo-B-HGD group from the fifth week of HGD feeding. The results in FIG. 5C show that the food intake by the Nogo-B-HGD group was increased, indicating that bodyweight change in Nogo-B-HGD mice is not related to the food intake.

Figure 6:
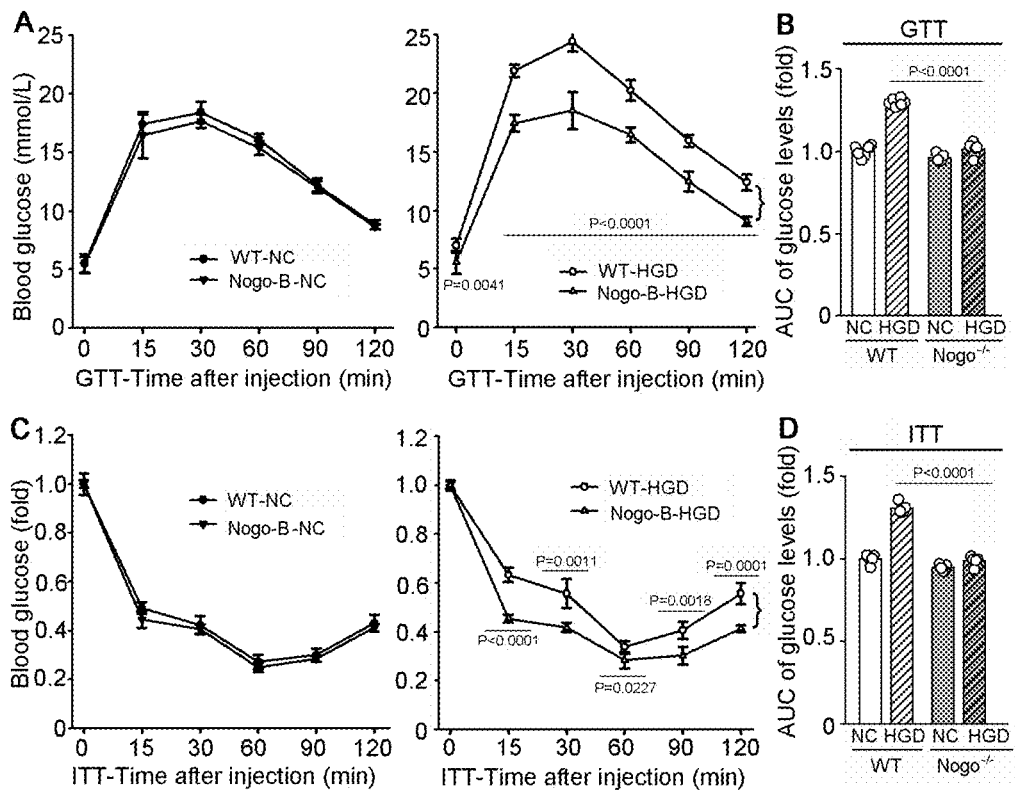
FIG. 6 shows the results of glucose tolerance test (GTT) and insulin tolerance test (ITT) of mice with inhibited Nogo-B expression by CRISPR/cas9 and control mice fed normal chow or the high-glucose diet for 9 weeks (GTT) or 10 weeks (ITT). Due to layout restrictions, Nogo in FIG. 6 represents Nogo-B.

FIG. 6 shows results of the glucose tolerance (GTT) and insulin tolerance (ITT) tests of the group of mice in which CRISPR/Cas9 technology was used to inhibit Nogo-B expression and the normal mouse group fed with normal chow or high-glucose diet for 9 weeks (for GTT) and 10 weeks (for ITT), respectively. Results show that the insulin sensitivity and glucose tolerance of normal mice fed the high-glucose diet (WT-HGD) were decreased. In contrast, no decreases of insulin sensitivity and glucose tolerance were observed in Nogo-B-HGD group.

Figure 7:
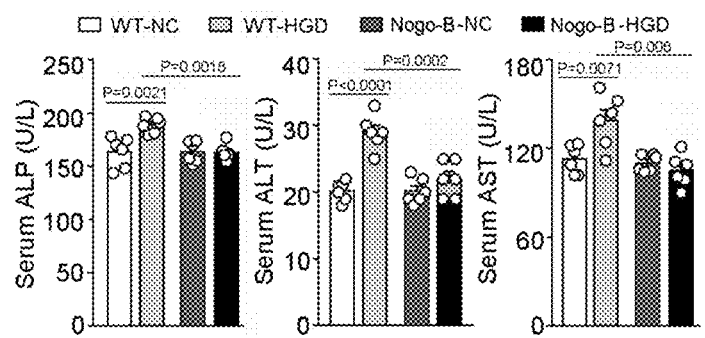
FIG. 7 shows the test results of enzyme activity in serum to characterizing liver function in mice with inhibited Nogo-B expression by CRISPR/cas9 and control mice fed normal chow or the high-glucose diet for 11 weeks.

FIG. 7 shows the test results of liver function enzyme activity in mice that CRISPR/Cas9 technology was used to inhibit Nogo-B expression and normal mice fed with normal chow or high-glucose diet for 11 weeks. As shown in the figure, normal mouse group fed with high-glucose diet (WT-HGD) had liver tissue damage, alkaline phosphatase ALP, alanine aminotransferase ALT, aspartate aminotransferase AST increased; while in mice group in which Nogo-B expression was inhibited fed with high-glucose diet (Nogo-B-HGD), these indicators were basically unchanged, indicating that high-glucose diet does not cause liver damage in mice in which Nogo-B expression was inhibited. WT-NC and Nogo-B-NC in the figure were liver function enzyme activity analysis of the mice group that CRISPR/Cas9 technology was used to inhibit Nogo-B expression and normal mice fed with normal chow, respectively, showing that inhibiting the expression of Nogo-B had no effect on the liver function enzyme activity of the mice.

Taken together, FIGS. 5-7 show that results of body-weight gain and GTT/ITT had no significant difference between the two groups of mice fed with normal chow, while the mice fed the high-glucose diet (WT-HGD) have abnormal glucose tolerance and insulin tolerance, and liver injury, increased ALP, ALT, AST levels, while the experimental results of glucose tolerance and insulin tolerance in the mice group in which Nogo-B expression was inhibited fed with high-glucose diet (Nogo-B-HGD) were close to those determined in the normal chow-fed group, and no injury was observed in the liver.

Example 4: Knockdown of Nogo-B Expression by siRNA Inhibits High-Fructose Diet (HFrD)-Induced Liver Injury The liver is the central organ of glucose and/or lipid metabolism, and targeting liver is more specific to regulate glucose and/or lipid metabolism. Examples 2 and 3 used CRISPR/cas9 technology to inhibit Nogo-B expression, which induces the systematic deficiency of Nogo-B expression. In order to verify the specific inhibition of Nogo-B expression in liver, we conducted the small interfering RNA experiment in mice.

In this Example, the sequences used were: si-Ctrl, UUCUCCGAACGUGUCACGUdTdT (SEQ ID NO: 15), ACGUGACACGUUCGGAGAAdTdT (SEQ ID NO: 16); si-Nogo-B, GGAUCUCAUUGUAGUCAUATT (SEQ ID NO: 5), UAUGACUACAAUGAGAUCCTT (SEQ ID NO: 6).

C57BL/6 mice were pre-fed HFrD for two weeks, then i.v. injected the pre-annealed control siRNA (si-Ctrl) or siRNA against Nogo (si-Nogo), respectively, from tail vein to specifically knockdown the liver Nogo-B expression using Engreen transfection reagent (Cat #: 18668-11-1, Engreen Biosystem Co., Ltd., Beijing, China) and strictly according to the manufacturer's instructions.

After siRNA injection and 12 h feeding, mice were subjected to fasting for 10 h followed by blood glucose test. Mice were then re-fed with high-fructose diet for 8 h and conducted another blood glucose test. After feeding high-fructose diet for 18 hours which is also 48 h after siRNA injection, all the mice were sacrificed, followed by collection of serum samples for subsequent experiments.

Figure 8:
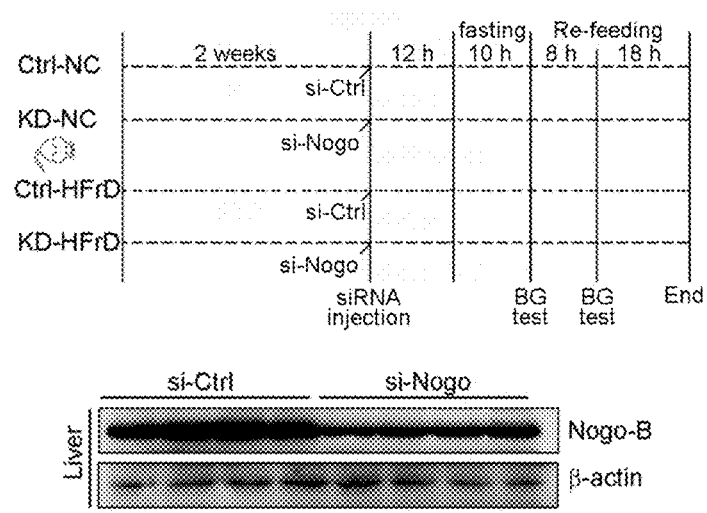
FIG. 8 shows model diagram of treatment in mice injected with siRNA against Nogo-B (si-Nogo-B) via tail vain to inhibit Nogo-B expression in the liver (si-Nogo-B group) or control siRNA (si-Ctrl group). After the mice were euthanized, the liver tissues were taken, and then Western blot was used to detect the expression level of Nogo-B in the mice liver. Due to the limitation of the layout, Nogo in the FIG. 8 represents Nogo-B.

As shown in FIG. 8, the four groups of mice were named as Ctrl-NC, KD-NC, Ctrl-HFrD and KD-HFrD, respectively, indicating that the control mice were fed normal chow (Ctrl-NC), the Nogo-B knockdown mice were fed normal chow (KD-NC), the control mice were fed HFrD (Ctrl-HFrD), and the Nogo-B knockdown mice were fed HFrD (KD-HFrD). The results in FIG. 8 show that at the protein level, the Nogo-B protein expression in the liver of si-Nogo-B group (group in which small interfering RNA was injected to targeted inhibition of Nogo-B expression) was decreased by about 50% compared with that in si-Ctrl group (group in which control small interfering RNA was injected), indicating that the knockdown efficiency of Nogo-B was about 50% and the knockdown was successful.

Figure 9:
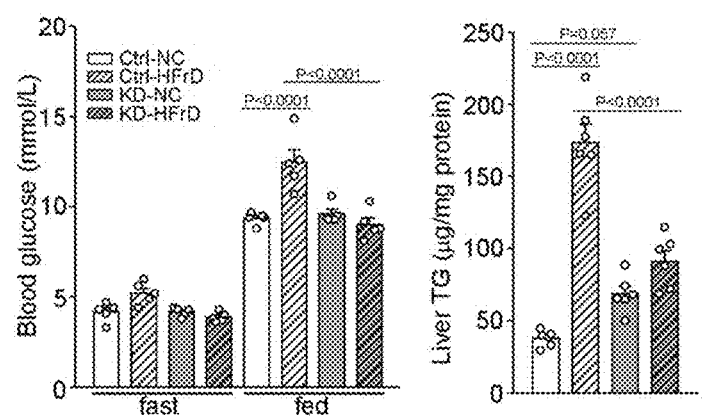
FIG. 9 shows detecting the fasting and non-fasting blood glucose levels and the liver triglycerides (TG) content of in mice for which siRNA technology was used to inhibit the expression of Nogo-B in the liver and in control mice (inject siRNA after feeding normal chow or high-fructose diet for 2 weeks).

FIG. 9 shows the results of fasting blood glucose and non-fasting blood glucose levels and liver triglyceride (TG) content in the liver of the mice in which the Nogo-B expression in the liver was inhibited by siRNA and the control mice (siRNA was injected after mice were fed high-fructose diet for 2 weeks). As shown in the figure, compared with group fed normal chow, high-fructose diet increased non-fasting blood glucose levels and liver TG contents in control mice (Ctrl-HFrD vs. Ctrl-NC). The non-fasting blood glucose levels and liver TG contents were close between the group of mice that Nogo-B expression was inhibited fed normal chow and HFrD and the corresponding group of control mice normal chow (KD-HFrD vs. KD-NC). The results of KD-NC and Ctrl-NC groups in the figure were blood glucose levels and liver TG levels of mice in which Nogo-B expression in the liver was inhibited by tail vein injection of si-RNA and control mice fed with normal chow, showing that the inhibition of liver Nogo-B expression has no effect on blood glucose levels, but mildly increased the liver TG level. This increase belongs to the benign category, because the biochemical indicators are normal (see FIG. 10). Nogo-B knockdown inhibited the excessive increase in liver TG levels caused by HFrD.

Figure 10:
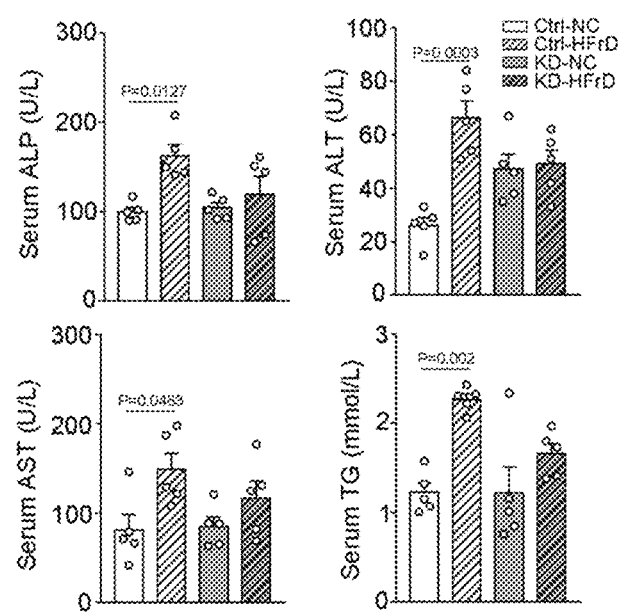
FIG. 10 shows the detection results of serum enzyme activities and serum TG levels in mice for which siRNA technology was used to inhibit Nogo-B expression in the liver and in control mice (inject siRNA after feeding normal chow or high-fructose diet for 2 weeks).

In addition, FIG. 10 shows the analysis results of the liver function enzyme activity and serum TG levels of the mice group in which the si-RNA technology is used to inhibit Nogo-B expression in the liver and the control mice group (fed with high-fructose diet 2 weeks in advance and then injected si-RNA). As shown in the figure, the liver tissues of the control mice group fed high-fructose diet (Ctrl-HFrD) were damaged, and the levels of alkaline phosphatase ALP, alanine aminotransferase ALT, aspartate aminotransferase AST were increased, and the serum TG level was increased. The mice group (KD-HFrD) in which Nogo-B expression in the liver was inhibited fed with high-fructose diet basically had no damage, and at the same time avoided the increase in serum TG level. In the figure, Ctrl-NC and KD-NC are the results of analysis of liver function enzyme activity and serum TG level in the mice group in which Nogo-B expression was inhibited by tail vein injection of si-RNA and control mice group fed with normal chow, showing that inhibition Nogo-B expression in mice liver has no effect on liver function enzyme activity and serum TG level.

Therefore, the results in FIG. 10 show that, consistent with Examples 2 and 3, knockdown of Nogo-B also inhibits the occurrence of liver injury caused by the high-fructose diet (serum ALP, ALT and AST activities reflect the degree of liver injury), and can antagonize the over increase of serum TG content.

The shown above is only the better embodiment of the invention and does not limit this invention. Any modification, equivalent replacement and improvement made within the spirit and principle of this invention shall be included in the protection scope of this invention.

The invention claimed is:

1. A medicine for treating disorders of glucose and/or lipid metabolism, wherein the medicine contains a Nogo-B inhibitor,
wherein the Nogo-B inhibitor is a nucleic acid molecule targeting Nogo-B for gene editing and further comprising a reagent for gene editing operation,
wherein the target DNA of the gene editing is exon 2 and exon 8 of Nogo-B gene, and wherein oligonucleotide sequences for the target DNA are selected from the group consisting of SEQ ID NO: 1, SEQ ID NO: 2, SEQ ID NO: 3, and SEQ ID NO: 4.

2. The medicine according to claim 1, wherein the Nogo-B inhibitor is an inhibitor for reducing Nogo-B mRNA level.

3. A method of treating glucose and/or lipid metabolic disorders, comprising administering to a subject the Nogo-B inhibitor of claim 1, thereby treating the glucose and/or lipid metabolic disorders.

4. The method according to claim 3, wherein the disorders of glucose and/or lipid metabolism are hyperlipidemia, diabetes, fatty liver, obesity, or arteriosclerotic cardiovascular or cerebrovascular disease.

* * * * *